April 5, 1932. L. BURBANK Plant Pat. 13
PLUM
Filed Sept. 23, 1930
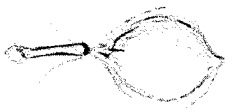
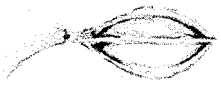
E. W. BURBANK
Executrix of
LUTHER BURBANK, Deceased.
By Robb & Robb
Attorneys

UNITED STATES PATENT OFFICE

LUTHER BURBANK, DECEASED, LATE OF SANTA ROSA, CALIFORNIA, BY ELIZABETH WATERS BURBANK, EXECUTRIX, OF SANTA ROSA, CALIFORNIA, ASSIGNOR TO STARK BRO'S NURSERIES & ORCHARDS COMPANY, OF LOUISIANA, MISSOURI

PLUM

Application filed September 23, 1930. Serial No. 483,935.

This invention relates to a new and distinct variety of plum.

This new variety of plum is a large, beautiful, pure golden freestone. Its appearance is striking and impressive. The size being pronounced, coupled with the clear yellow, thin, finely textured skin, causes its individual characteristics to be outstanding and unusual. Although the skin is very thin, tests have proven it to possess wonderful keeping and shipping qualities. The flesh is similar to the skin in color, being modified only by the translucent appearance. When mature, the skin is removed very easily from the flesh. The mild sub-acid richness of the fruit permeates the flesh rather evenly, and near the seed the acidity becomes slightly greater.

The attached drawings and specification to follow show the distinctions and characteristics of this variety of plum which has been asexually reproduced.

*Young trees in nursery row*

*Tree.*—The young trees are vigorous, divergent to spreading branching habit with forks acute to obtuse. The older bark becomes scaly, dull brown with gray scarfskin and irregular numerous gray-brown lenticels, transversely elongated, often merging into the longitudinal bark cracks.

*Twigs.*—The twigs are moderately slender with internodes of medium length. The bark is rather smooth and glossy on older portions, showing an undercolor or absinthe green, greatly modified by gray-brown lenticels and other markings. The more exposed portions of the twigs are strongly colored tawny olive brown shading to ochre red and dark vinaceous red. The dormant buds are very small but with projecting leaf-scars which are rather prominent.

*Foliage.*—The leaf on normal new growth is medium sized to rather small, the blade measuring about 3½ inches long and 1½ inches wide with an oval shape, the base and apex describing nearly the same angle (80° to 90°). The texture is rather heavy; margin oddly irregular, double or triple—cerrate with minute reddish glandular tips. The upper surface is glossy and wrinkled with sides of the blade wavy; color is forest green. The lower surface is glabrous, roughened by the prominent and numerous veins; the midrib has a slight brownish pubescence at the sides; color modified to bice green or lighter by a surface layer of white cells.

*Petiole.*—The petiole is rather stout, smooth, grooved on upper side and about ½ inch long, with a vinaceous red coloring, often extending to the midrib.

*Glands.*—There are four to six glands with partly developed glands at the base of the blade; form is globose; the color is the same as the petiole modified by a yellowish tinge. (The above colors are in accordance with Ridgeway's Color Standard.)

*Full grown trees*

*Tree.*—The tree's growth is moderately vigorous; branching habit extreme upright at first but developing an open head. The branches are stiff and strong; forks very acute, 15 to 20 degrees from vertical. The older bark is rough, cross checks becoming almost complete circles around the larger limbs, and exfoliation very moderate and slow. The bark resembles that of smaller oak branches.

*Foliage.*—The form of the leaf is broadly obovate inclined to oval; is large to very large, measuring from base to apex about 4 to 4½ inches in length, and 2¼ to 2½ inches in width. The heavy texture is somewhat leathery. The upper surface is smooth, colored dark green with veins and midrib sunken. The lower surface is smooth and is several shades lighter green than the upper surface, showing light rayish pubescence near the midrib where it is not exposed to weathering. The midrib is prominent and almost white. The veins are also prominent and of light green color. The base is acute. The margin is doubly serrate with slightly rounded points; apex is prominent acute. There are usually two, but sometimes three glands, which are small and round, with first serration often almost glandular.

*Petiole.*—The petiole is fairly heavy, grooved, about ¾ inch long, and sometimes tinged with brownish red.

*Twig.*—The twig is swollen at the base of the prominent brown leaf and fruit buds. The leaf scars are rather large. The bark on the new growth is glossy, green, and with brown shading on the exposed surface.

*Fruit*

*Form.*—The shape is generally roundish with a slight tendency to cordate. The plum is large with an axial diameter about 1¾ inches; larger transverse diameter is about 1⅞ inches while the smaller transverse diameter measures about 1¾ inches. The stem is short and rather slender, being slightly enlarged at insertion. The cavity is regular, being moderately wide and deep. The suture begins at the stem and runs almost to the apex which is rounded and not prominent.

*Color.*—The skin is a clear apricot yellow deepening slightly with full maturity. There are small, submerged, green dots which are noticeable only on the exposed side. The surface has occasional flecks of russet, and the bloom is very thin, white.

*Skin.*—The skin is very thin but not easily broken, and is readily removed from the flesh when fully mature.

*Stone.*—The stone is small in comparison with the size of fruit, measuring about ¾ inch in length, ⅝ inch in width and ⅜ inch thick. The ventral suture is slightly grooved while the dorsal suture is strongly grooved with distinct ridges or protuberances on the side near the stem end. The base is obtuse; the apex broadly acute.

*Flesh.*—The flesh is a clear yellow, almost the same color as the skin, being modified only by the translucent appearance. The texture is fine, smooth, almost melting, is moderately juicy with a rich, mild sub-acid flavor, slightly aromatic (The colors are in accordance with Ridgeway's Color Standard.)

The specifications herein manifest the general characteristics of the plum, yet it is understood they vary slightly due to soil or climatic conditions.

What is claimed is:

The plum tree herein described, characterized by the clear golden yellow color of the skin of its fruit, as shown.

In testimony whereof I affix my signature.

ELIZABETH WATERS BURBANK,
*Known also as Elizabeth Burbank, Executrix of Luther Burbank, Deceased.*